United States Patent [19]
Kullenberg et al.

[11] Patent Number: 5,809,104
[45] Date of Patent: Sep. 15, 1998

[54] METHOD AND DEVICE FOR MEASURING THE CONTENT OF BONE MINERAL IN THE SKELETON

[76] Inventors: Ragnar Kullenberg, Pålsbovägen 9F, S-302 74 Halmstad; Anders Ullberg, Berghällavägen 4, S-616 33 Åby, both of Sweden

[21] Appl. No.: 875,136
[22] PCT Filed: Jan. 10, 1996
[86] PCT No.: PCT/SE96/00008
§ 371 Date: Jul. 10, 1997
§ 102(e) Date: Jul. 10, 1997
[87] PCT Pub. No.: WO96/21856
PCT Pub. Date: Jul. 18, 1996

[30] Foreign Application Priority Data

Jan. 12, 1995 [SE] Sweden .................................. 9500089

[51] Int. Cl.⁶ .................................................. G01N 23/02
[52] U.S. Cl. ................................................. 378/54; 378/56
[58] Field of Search ................................. 378/54, 56, 51, 378/53, 95

[56] References Cited

U.S. PATENT DOCUMENTS

| | | |
|---|---|---|
| 4,663,772 | 5/1987 | Mattson et al. . |
| 4,768,214 | 8/1988 | Bjorkholm . |
| 4,811,373 | 3/1989 | Stein ......................................... 378/54 |
| 4,829,549 | 5/1989 | Vogel et al. ........................... 378/54 X |
| 5,204,888 | 4/1993 | Tamegai et al. ....................... 378/54 X |
| 5,247,559 | 9/1993 | Ohtsuchi et al. ...................... 378/54 X |
| 5,348,009 | 9/1994 | Ohtomo et al. . |
| 5,712,892 | 1/1998 | Weil et al. ................................ 378/54 |

FOREIGN PATENT DOCUMENTS

| | | |
|---|---|---|
| 432 730 | 6/1991 | European Pat. Off. . |
| 549 858 | 7/1993 | European Pat. Off. . |
| 42 14 369 | 11/1992 | Germany . |
| 1546926 | 5/1979 | United Kingdom . |
| WO 86/07531 | 12/1986 | WIPO . |

*Primary Examiner*—David P. Porta
*Attorney, Agent, or Firm*—Merchant, Gould, Smith, Edell, & Schmidt, P.A.

[57] ABSTRACT

The invention concerns a method and arrangement for measuring the bone mineral content in the skeleton in a body part, which is irradiated from one side with X-radiation which is detected on the opposite side of the body part. The X-radiation has two energy levels, the detected radiation is analyzed and the thickness of the body part is determined. The analysis takes account of the thickness of the body part and in order to calibrate the measuring process, a reference object of known composition is measured. The arrangement comprises: means (3) for generating X-radiation at two energy levels which means is disposed on one side (2a) of a casing (2) whose shape is adapted to that of the body part and which means is directed towards the latter. A radiation-detector matrix (4) disposed on the opposite side (2b) of the casing detects the X-radiation received. The distance-measuring devices (50 are coupled with an image and signal-processing unit (7) and are disposed inside the casing (2) on opposite sides of said body part. The image and signal-processing unit (7) is arranged such that the bone mineral content is determined by a combination of the signals recorded in the detector matrix (4) and the signals received from the distance-measuring devices (5) with respect to the measurement on the body part and the measurement on the reference object of known composition.

3 Claims, 4 Drawing Sheets

METHOD AND DEVICE FOR MEASURING THE CONTENT OF BONE MINERAL IN THE SKELETON

The present invention concerns a method of measuring the bone mineral content in the skeleton in a body part which is irradiated from one side with X-radiation which is detected on the opposite side of the body part.

The present invention also concerns an arrangement for measuring the bone mineral content in the skeleton in a body part.

An illness which is rapidly increasing throughout the world is osteoporosis, both in the industrialized world and in developing countries. The illness generally affects older women but it has recently been discovered that osteoporosis can also affect younger people and people of both sexes.

In order to reduce the risk of this type of illness, it is usual to give older women in particular drugs which have an inhibiting effect on the decalcification of the skeleton. At present the administration of this medication is somewhat arbitrary since with existing methods and arrangements it is difficult and expensive to assess whether medication is necessary. Consequently large quantities of drugs are prescribed to people who are not in fact suffering from osteoporosis whilst others who in reality are suffering from it do not receive the help they require. This gives rise both to unnecessary personal suffering and unnecessary costs for society. In order to overcome this problem, it has proved necessary to be able to diagnose osteoporosis reliably.

The best way of establishing whether a person is suffering from osteoporosis is to determine the bone mineral content in any suitable bone in the body. A large number of different devices have been developed for this purpose.

WO-A-86/07351 discloses an arrangement for measuring the bone mineral content in the heel bone. This measuring arrangement has a casing in one side of which a source of gamma or X-rays is disposed together with a radiation-detection device disposed on the side opposite the X-ray source. The detection device is in turn connected to some type of control system, for example a computer which analyzes the results obtained. In order that the arrangement can function to a relatively satisfactory degree, it is necessary for the space, in the casing, surrounding the foot to be filled with water. In spite of this, however, the results provided by the arrangement are unsatisfactory.

U.S. Pat. No. 5,348,009 discloses a similar arrangement for measuring the bone mineral content, in which arrangement a radiation source is disposed on one side of a casing adapted, for example, to a foot. Disposed on the opposite side is a detector which is connected to a signal-processing unit. In addition devices for measuring distance are disposed in the casing on each of its sides around the object to be measured in order to determine the thickness of the bone. These devices are also connected to the signal-processing unit, and the mineral content per unit of volume can be determined by a combination of the signals received from the radiation detector and the thickness measurement.

EP-A-0 432 730 discloses a further measuring arrangement for measuring the bone mineral content. This arrangement comprises a casing, a device disposed on one side of the casing for generating X-radiation together with means for detecting X-radiation. The arrangement also comprises a filter which is disposed in front of the X-ray device and can vary such that the spectrum of the X-ray signal is delimited, whereby the X-ray signal is divided into two different energy levels. A disadvantage of this method is hat the bone mineral content is established only on the basis of the measurements received from the two different levels of the X-ray signal such that it is impossible to separate all the components of the heel and the method does not provide reliable results about the cause.

Finally EP-A-0 549 858 discloses an arrangement for carrying out measurements of bone mineral contents wherein an X-ray source having two energy levels or energy bands is used to determine the amount of a given substance in a physical object. The bone mineral content sought can supposedly be obtained as a result of the fact that the invention uses a special calculation method by means of which given components which are undesirable for the result are eliminated. However this method also provides highly unreliable results and in the worst case sick patients can be diagnosed as healthy.

U.S. Pat. No. 5,348,009 and GB-1 546 926 are also relevant prior art in this domain.

The object of the present invention is to overcome the problem associated with the prior art X-ray type bone mineral measuring arrangements and to propose a method for measuring the bone mineral content of the skeleton in a simple and reliable manner. This object is achieved by the following combination: the irradiation with X-rays is carried out at two energy levels, the detected radiation is analyzed, the thickness of the body part is determined, when the detected radiation is analyzed, account is taken of the thickness of the body part and, in order to calibrate the measuring process, it is performed with a reference object of known composition.

According to a particular characteristic of the invention, the thickness of the body part is determined by measuring a distance between an X-ray source and the body part and between the latter and a detector matrix, the thickness of the body part being determined by comparing these distances and the distance between the radiation source and the matrix.

In the arrangement according to the invention the method is carried out in that the arrangement comprises a combination of a means which generates X-radiation at two energy levels and which is disposed on one side of a casing whose shape is adapted to that of the body part and which means is directed towards the latter, a radiation detector matrix being disposed on the opposite side of the casing in order to detect the X-radiation from said means; an image and signal-processing unit to which the matrix is connected for analyzing the signals recorded in the detector matrix; distance-measuring devices (5) which are coupled to the image and signal-processing unit are disposed inside the casing on opposite sides of said body part, the image and signal-processing unit being arranged such that, by combining the signals recorded in the detector matrix and the signals obtained from said distance-measuring devices with respect, on the one hand, to the measurement on the body part and, on the other, to the measurement on a reference object of known composition, the bone mineral content in the skeleton of the body part is established.

In the following the invention will be described in greater detail with reference to the drawings, in which.

Figure 1:
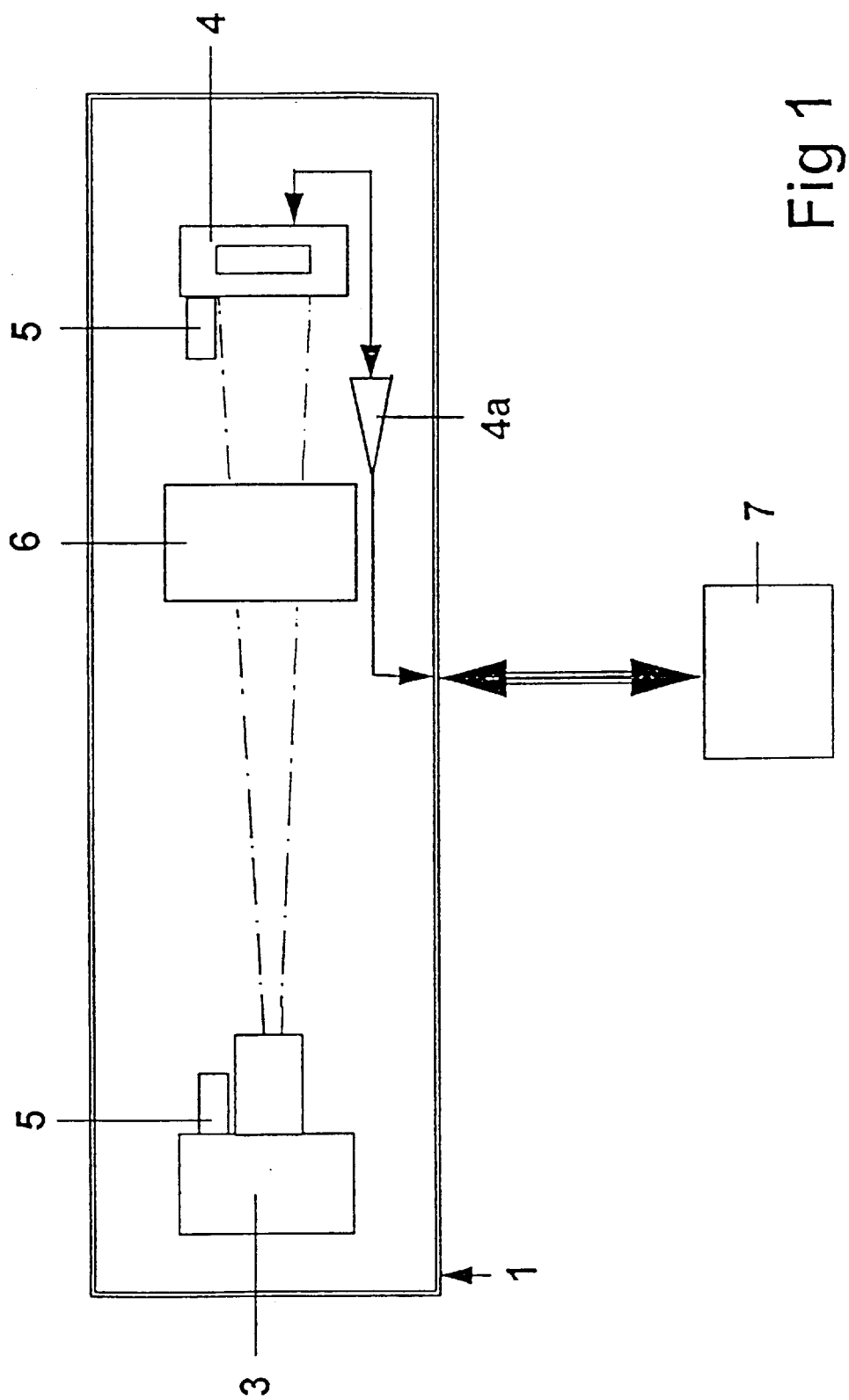
FIG. 1 shows an outline diagram of the main components of the bone mineral measuring device.

The arrangement according to the invention substantially comprises a measuring unit 1 and an image and signal-processing unit 7. The measuring unit 1 is formed by a casing 2 which is adapted to the shape of a body part and in whose one side 2a is disposed a radiation source 3 for radiation at two energy levels and in whose other side 2b a radiation detector matrix 4 is disposed for detecting the radiation emitted from the radiation source 3.

The radiation source 3 is preferably formed by an X-ray tube which can emit photons at two separate energy levels, for example 30 kV and 75 kV. These energy levels are used to determine the bone mineral content of the object to be measured 6 and it is therefore important that the energy levels are clearly separated and clearly defined. The different energy levels can, for example, be brought about by driving the X-ray tube 3 with a generator which can vary between energy levels. Another way of producing X-radiation at two energy levels is to filter the radiation obtained from an X-ray source 3 at one energy level.

The radiation detector matrix 4 for detecting radiation is disposed in an opposite position relative to the radiation source 3. The detector matrix 4 comprises a number of elements which are arranged in matrix form and which can detect and quantify the radiation which impinges on each point at a given incidence or within a given time.

The X-ray tube 3 and the detector matrix 4 can either be stationary or describe a linear movement over the object to be measured 6. In both cases a collimator is disposed connected to the X-ray tube 3, whereby the divergence of the X-rays can be delimited to cover the range of vision of the detector matrix 4.

When the X-ray tube 3 is disposed in the stationary position, a specially arranged collimator is mounted in front of the detector matrix 4. The collimator is constructed such that it is perforated by apertures whose number equals that of the individual elements in the radiation detector matrix lying therebehind. The orientation on the apertures is such that they diverge from the focus of the radiation source and each aperture is oriented towards each of its points on the detector matrix. The purpose of the collimator is to filter out scattered secondary radiation which can cause interference, to operate such that the beams which pass through the apertures remain parallel, and to direct the transmitted radiation towards respective points on the detector matrix. The collimator can be made of material which has such high attenuation that only the beams which pass through the apertures are detected by the detector matrix 4 lying therebehind.

In an alternative embodiment, in which the X-ray tube 3 is made to carry out a linear movement over the object to be measured 6, the X-ray tube 3 is mounted on a mechanical arm. This arm moves in relation to the body part 6 to be measured such that the sections of the body part which are essential to the measurement are scanned. If the detector 4 is arranged so as to move with the X-ray tube, the detector matrix 4 can comprise a single detector element.

Figure 2:
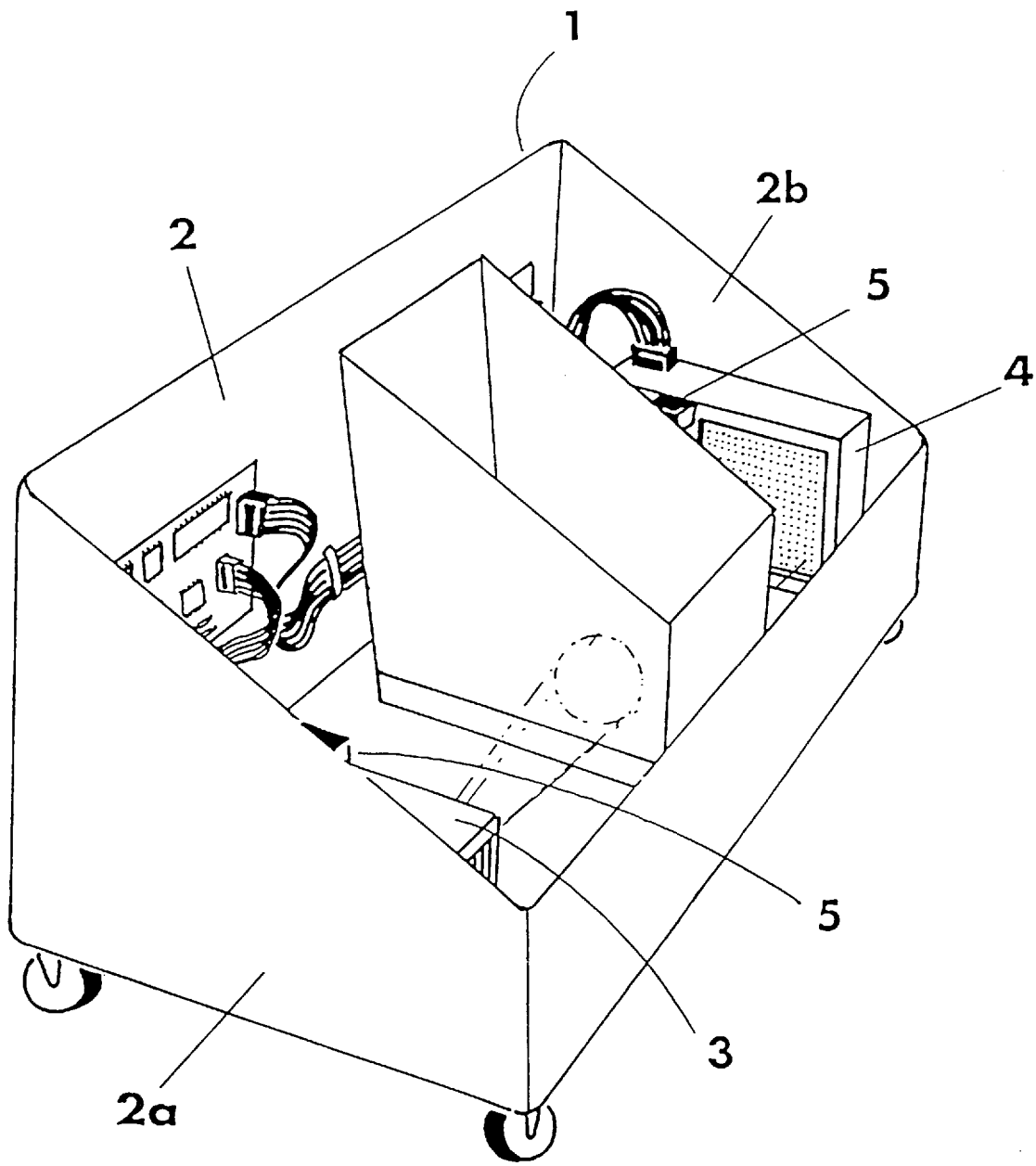
FIG. 2 shows a perspective view of the measuring unit, the top of the casing being omitted.

In the case of the embodiment shown in FIG. 2 the measurement of the bone mineral content is carried out in a heel bone. The X-ray tube 3 is disposed so as to scan an area of approximately 10.0×15.0 cm, i.e. equivalent to the total size of the heel bone. When the foot to be measured is placed in the casing 2. The X-ray tube 3 is directed towards the one side of the foot, towards or in the region of the heel part of the foot. The size of the region which the X-ray tube 3 scans obviously depends on the size of the body part 6 to be measured.

The measuring unit further comprises a computer/amplifier 4a in order to quantify the radiation towards the detector matrix 4. The computer 4a is arranged such that it can identify at which point on the detector matrix 4 the radiation impinges and the photon energy level in the radiation. Since two "measuring windows" are used in the case of the energy levels characteristic of the two voltages generated, a more reliable result is obtained.

The unit bearing reference sign 6 symbolizes the body part to be measured, such as a heel bone or a forearm, for example. In the case of the embodiment of a bone mineral measuring device shown in FIG. 2, the device is arranged for measuring the heel part of a foot.

In order that the principal components of the heel, water, fat and bone mineral, can be clearly determined, a third measuring parameter is required. This is obtained in that the distance measuring devices 5 are arranged on each side of the body part 6 to be measured and the distance from each side of the X-rayed object 6 can be determined by means of these devices 5. The thickness of the object can thus be calculated. These devices 5 are preferably made of laser measuring rings. In order that the position of the foot in the casing does not lead to unreliable measuring results, the distance-measuring devices 5 are arranged on each side of the foot.

The method and arrangement according to the invention are based on the fact that, by means of the above-described X-radiation and measuring of the thickness of the object, three measurements can be provided which are different from one another and by means of which the proportion of bone mineral in a body part can be established.

The object or body part to be measured substantially consists of three components: bone mineral (in the form of hydroxyapatite $Ca_{10}(PO_4)_6(OH)_2$), fat and water. The parameters which concern these components are designated b, f and s, respectively, in the following.

When the object to be measured is irradiated with X-radiation at two energy levels, the following equations can be laid down:

$$N_1 = N_{01} \exp(-\mu_{b1} t_b \rho_b - \mu_{s1} t_s \rho_s - \mu_{f1} t_f \rho_f) \qquad (1)$$

$$N_2 = N_{02} \exp(-\mu_{b2} t_b \rho_b - \mu_{s2} t_s \rho_s - \mu_{f2} t_f \rho_f) \qquad (2)$$

The X-radiation at the lower energy level (for example 35 kV) is given the index 1 and the X-radiation at the higher energy level (for example 70 kV) is given the index 2. $N_i$ is the measured computing speed after passing through the object at energy level i; $N_{0i}$ is the measured computing speed outside the object at energy level i; $\mu_{xi}$ is the mass attenuation coefficient ($cm^2/g$) for the respective component; $t_x$ is the thickness (in cm) of the respective component and $\rho_x$ is the density of the respective component.

The total thickness of the object is determined by means of distance-measuring devices on both sides of the object.

$$T = t_b + t_s + t_f \qquad (3)$$

in which T represents the total thickness of the object and $t_b$, $t_s$ and $t_f$, respectively, represent the thickness of each component.

In order to be able to calculate the thickness from equations (1) and (2), the computing speeds outside the object, $N_{01}$ and $N_{02}$, must be determined. This is achieved by placing an object of known composition in the arrangement. $N_{01}$ and $N_{02}$ can then be determined as:

$$N_{01} = N_{1F} \exp(-\mu_{b1} t_{bk} \rho_b - \mu_{s1} t_{sk} \rho_s) \qquad (4)$$

$$N_{02} = N_{2F} \exp(-\mu_{b2} t_{bk} \rho_b - \mu_{s2} t_{sk} \rho_s) \qquad (5)$$

in which $N_{1F}$ and $N_{2F}$ are the measured computing speeds of the lower and higher energy levels, respectively, in the radiation after passing through the object of known composition.

The mass attenuation coefficients, the densities and thicknesses ($t_{bk}$, $t_{sk}$) are known quantities. The thicknesses of the different components can therefore be calculated from the different equations for each element of the detector matrix. A representation of the bone mineral content of the body part to be measured can be produced from the result from each of these elements.

In order to evaluate the results obtained in the detector matrix 4 and in the distance-measuring devices 5 an image and signal-processing unit 7, preferably a personal computer, is used.

The measured quantitative values of the radiation at both photon energy levels are used to calculate the algorithms essential for assessing the result. Preferably the device also has access to databases containing standard values calculated from measured values from a large number of different specimens. The value measured by the measurement is compared with the value stored in the database in order to determine whether decalcification of the skeleton exists.

The computer is equipped with software adapted to the object, whereby the combinations of information from the detector matrix and information from the distance-measuring devices are used such that all the components of the foot, fat, water and bone mineral, can be determined with a high degree of accuracy.

A keyboard is used to communicate with the computer unit so that the operator can control the various possible operations.

A screen on which images of the measured object can be displayed is preferably used for displaying the result. A printer can also be used to produce print-outs of the result obtained.

Figure 3:
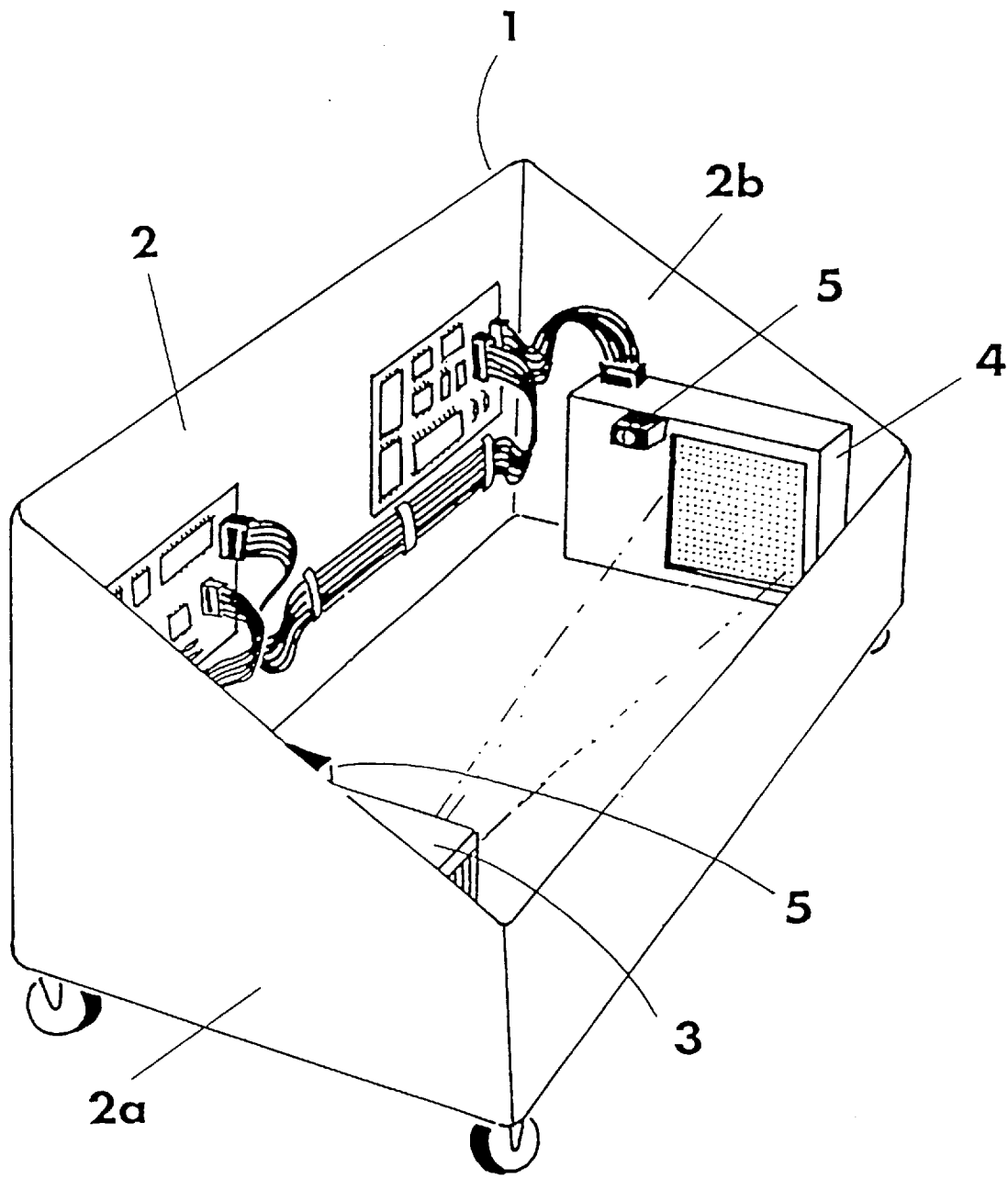
FIG. 3 shows a perspective view of the measuring unit according to FIG. 2, the shield for the body part also being omitted.

FIGS. 2 and 3 show the most preferable embodiment of the arrangement according to the invention, which is an apparatus adapted for measuring a heel bone. For this application the measuring apparatus can be constructed such that it is relatively small and simple so that the apparatus can be easily be moved for measuring different patients in different environments.

Figure 4:
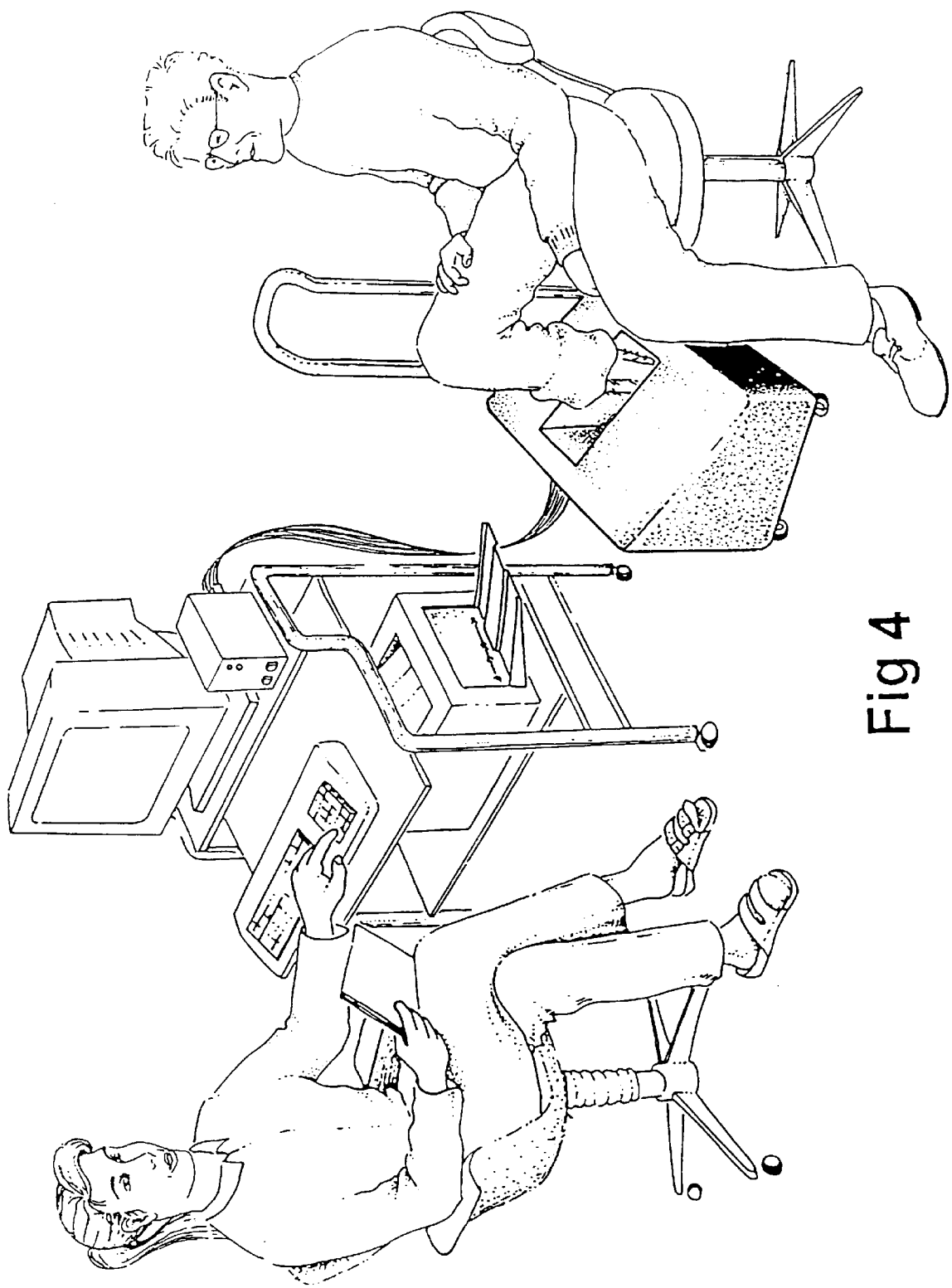
FIG. 4 shows an application of the arrangement according to the invention for measuring the bone mineral content.

The invention is in no way restricted to the embodiment shown in FIGS. 2 to 4. The principles of the invention can be adapted to any type of bone found in any part of the body which is large enough to be measured. The invention is restricted merely to the content of the following claims, it being clear that a person skilled in the art can perform the method according to the invention in a large number of different arrangements within the scope of the inventive concept.

We claim:

1. Method of measuring the bone mineral content in the skeleton in a body part which is irradiated from one side with X-radiation which is detected by a detector matrix (4), comprising a number of elements which are arranged in matrix form on the opposite side of the body part, characterized by the combination of the following irradiation with X-rays occurs at two energy levels; the detected radiation is analyzed; the thickness of the body part is determined; the analysis of the detected radiation takes account of the thickness of the body part in order to determine the principal components of the bodypart, water, fat and bone mineral to thereby produce a representation of the bone mineral content in the skeleton in said body part and the intensity of the X-radiation is determined by measuring a reference object of known composition.

2. Method according to claim 1, characterized in that the thickness of the body part is established by measuring a distance between an X-ray source (3) and the body part and between the latter and the detector matrix (4), the thickness of the body part being determined by comparing these distances with the distance between the radiation source (3) and the matrix (4).

3. Arrangement for measuring the bone mineral content in the skeleton in a body part, characterized in that the arrangement comprises a combination of: means (3) arranged to generate X-radiation at two energy levels and which is disposed on one side (2a) of a casing (2) whose shape is adapted to that of the body part and which means is directed towards the latter, a radiation-detector matrix (4) comprising a number of elements, which are arranged in matrix form being disposed on the opposite side (2b) of the casing in order to detect X-radiation from said means (3); an image and signal-processing unit (7) to which the matrix (4) is connected for analysis of the signals recorded in the detector matrix (4); distance-measuring devices (5) coupled with the image and signal-processing unit (7) are disposed inside the casing (2) on opposite sides of said body part, the image and signal-processing unit (7) being arranged such that the bone mineral content in the skeleton in the body part is determined by determining the thickness of the components bone mineral, water and fat by a combination of the signals recorded in the detector matrix (4) and the signals received from the distance-measuring devices (5) with respect to the measurement on the body part and the measurement on the reference object of known composition.

\* \* \* \* \*